United States Patent [19]

Müller

[11] Patent Number: 4,847,013

[45] Date of Patent: Jul. 11, 1989

[54] PROCESS FOR THE PREPARATION OF N-PHOSPHONOMETHYLGLYCINE

[75] Inventor: Wolf-Dieter Müller, Hofheim am Taunus, Fed. Rep. of Germany

[73] Assignee: Hoechst Aktiengesellschaft, Frankfurt am Main, Fed. Rep. of Germany

[21] Appl. No.: 210,817

[22] Filed: Jun. 24, 1988

[30] Foreign Application Priority Data

Jun. 27, 1987 [DE] Fed. Rep. of Germany ....... 3721285

[51] Int. Cl.⁴ .............................................. C07F 9/38
[52] U.S. Cl. .................................................... 562/17
[58] Field of Search ................... 210/502.5 F

[56] References Cited

U.S. PATENT DOCUMENTS

| | | | |
|---|---|---|---|
| 3,956,370 | 5/1976 | Parry et al. | 260/502.5 F |
| 4,233,056 | 11/1980 | Maier | 260/502.5 F |
| 4,442,041 | 4/1984 | Subramanian | 260/502.5 F |
| 4,650,613 | 3/1987 | Palmer et al. | 260/502.5 F |

FOREIGN PATENT DOCUMENTS

| | | | |
|---|---|---|---|
| 55695 | 7/1982 | European Pat. Off. | 260/502.5 F |
| 0187633 | 7/1986 | European Pat. Off. | |
| 216745 | 4/1987 | European Pat. Off. | 260/502.5 F |

*Primary Examiner*—J. E. Evans

*Attorney, Agent, or Firm*—Curtis, Morris & Safford

[57] ABSTRACT

The invention relates to a process for the preparation of N-phosphonomethylglycine of the formula I

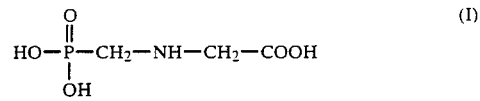

(I)

wherein a compound of the formula II or salts and esters thereof

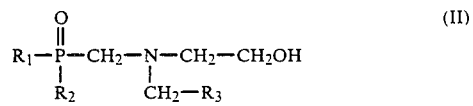

(II)

in which $R_1$ and $R_2$ denote hydroxyl or a hydrolyzable group and $R_3$ denotes aryl, is reacted in a closed reaction vessel in the presence of a dehydrogenation catalyst and a hydrogenation catalyst with an alkali metal hydroxide or alkaline earth metal hydroxide in water as the solvent and, when the reaction has ended, a mineral acid is added to liberate N-phosponomethylglycine from its salt.

10 Claims, No Drawings

PROCESS FOR THE PREPARATION OF N-PHOSPHONOMETHYLGLYCINE

The present invention relates to a novel process for the preparation of N-phosphonomethylglycine.

N-phosphonomethylglycine is known by the name glyphosate. Glyphosate and a large number of its salts are of major economic importance as herbicides.

A large number of processes for the preparation of N-phosphonomethylglycine have already been published. One of these methods is described in U.S. Pat. No. 4,442,041. In this process, N-(diethylphosphonomethyl)iminobisethanol is reacted with concentrated aqueous alkali metal hydroxide in the presence of cadmium oxide or zinc oxide. After acidification, N-phosphonomethylglycine is obtained in a yield of about 33%. In addition to the low product yield, a further disadvantage of this process is the fact that high reaction temperatures of about 270°-280° C. are required. Thermal dealkylation of N-alkyl-N-phosphonomethylglycine to give N-phosphonomethylglycine is furthermore described in EP-A No. 0,187,633. However, high reaction temperatures of 250°-350° C. are also required in this process.

A combined dehydrogenation and hydrogenation process for the preparation of glyphosate starting from N-benzyl-N-phosphonomethylaminoethanol which, surprisingly, can be carried out at relatively low temperatures has now been found.

The present invention thus relates to a process for the preparation of N-phosphonomethylglycine of the formula I

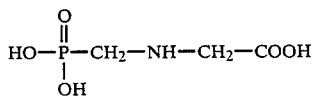
(I)

which comprises reacting an N-benzyl-N-phosphonomethyl-aminoethanol derivative of the general formula II or salts and esters thereof

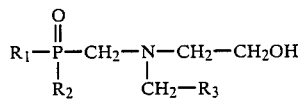
(II)

in which $R_1$ and $R_2$ independently of one another denote hydroxyl or a hydrolyzable group, such as $(C_1-C_6)$alkoxy, $(C_3-C_6)$ cycloalkoxy, aryloxy, aryl$(C_1-C_4)$alkoxy, mercapto, $(C_1-C_6)$alkylthio, $(C_3-C_6)$cycloalkylthio, arylthio, aryl$(C_1-C_4)$alkylthio, amino, mono- or di$(C_1-C_6)$alkylamino, arylamino or aryl$(C_1-C_4)$alkylamino and $R_3$ denotes aryl, in a closed reaction vessel in the presence of a dehydrogenation catalyst and a hydrogenation catalyst with an alkali metal hydroxide or alkaline earth metal hydroxide in water as the solvent and, when the reaction has ended, adding a mineral acid to liberate N-phosphonomethylglycine from its salt.

The alkyl groups contained in the above alkoxy, alkylthio or alkylamino radicals can be straight-chain or branched. They denote, for example, methyl, ethyl, propyl, isopropyl, buty or hexyl.

The term aryl used above includes phenyl or substituted phenyl which contains, in particular, 1 to 3 substituents from the group comprising $(C_1-C_4)$alkyl, $(C_1-C_4)$alkoxy, or halogen, preferably $(C_1-C_4)$alkyl. Examples of substituted phenyl are the radicals methylphenyl, butylphenyl, methoxyphenyl, butoxyphenyl, fluorophenyl, chlorophenyl, dimethylphenyl, dichlorophenyl, methylchlorophenyl, dimethoxyphenyl, trimethylphenyl and ethyldichlorophenyl. For economic reasons, hydroxyl and $(C_1-C_4)$alkoxy, preferably methoxy or ethoxy, are most suitable for the radicals $R_1$ and $R_2$, and phenyl, which can be substituted by $(C_1-C_4)$alkyl, especially phenyl, is most suitable for $R_3$; however, the nature of the radicals $R_1$, $R_2$ or $R_3$ is not critical for carrying out the process.

Dehydrogenation catalysts which can be used are the catalysts which are known per se for dehydrogenation reactions, for example cadmium oxide, zinc oxide, copper or copper/zirconium mixed catalysts, and hydrogenation catalysts which can be used are catalysts which are known per se for hydrogenation, such as palladium, platinum, rhodium, iridium, ruthenium, nickel or cobalt. Combinations of copper or copper/zirconium mixed catalysts with palladium, platinum or nickel are preferred, and copper in combination with palladium or platinum is particularly preferred.

The dehydrogenation of aminoalcohols to give aminocarboxylic acids and the hydrogenolysis of benzyl groups are in each case known as such from British Pat. No. 2,148,287 and Org. Reactions Vol. VII, John Wiley & Sons, N.Y. 1953.

However, it is surprising that the dehydrogenation can be linked to the hydrogenation without problems. Half of the hydrogen obtained during the dehydrogenation accordingly reacts further in situ on the same molecule, so that no addition of hydrogen is necessary. It is also surprising that the alcohols, thioalcohols or amines formed by hydrolysis during the alkaline reaction procedure do not impair selective dehydrogenation of the hydroxymethyl group of the N-benzyl-N-phosphonomethylaminoethanol derivatives of the formula II.

Alkali metal hydroxides and alkaline earth metal hydroxides which can be used in the process according to the invention are lithium hydroxide, sodium hydroxide, potassium hydroxide or calcium hydroxide. The alkali metal hydroxides are preferably used, sodium hydroxide, being especially preferred. The molar ratio of the alkali metal or alkaline earth metal hydroxide to the compound of the formula II in the reaction mixture should be greater than or equal to 3; a molar ratio of 3–4.5:1, in particular 3.3:1 to 3.8:1, is preferred. The alkali or alkaline earth metal hydroxide can be added to the reaction mixture in bulk, but is preferably added in case of the alkali metal hydroxide in the form of a concentrated aqueous solution.

The water used as the solvent can be added directly or in the form of the abovementioned alkali metal hydroxide solutions.

The reaction takes place within a wide temperature range. The reaction temperature is preferably in a range from 120° C. to 200° C., in particular in the range from 160°-180° C. The upper limit for the temperature is determined by the thermal stability of the components present in the reaction mixture.

The process is advantageously carried out in an autoclave. A pressure builds up in the autoclave during the reaction also as a result of the formation of hydrogen, its level being determined by the dimensions of the autoclave, in particular from the ratio of the reaction volume to the autoclave volume. The pressure as a rule varies between 1 and 50 bar. Since the upper pressure limit for the reaction is not critical, the reaction can also be carried out under higher pressures.

As described above, under the strongly alkaline reaction conditions, hydrolysis of the phosphonic acid derivative part structure to the phosphonic acid di-alkali metal salt takes place in parallel with the linked dehydrogenation/hydrogenation. This hydrolysis can equally well be carried out partly or completely before the start of the linked dehydrogenation/hydrogenation by reacting the N-benzyl-N-phosphonomethyl-aminoethanol derivative with the corresponding amount of alkali metal hydroxide before the start of the reaction.

The strongly alkaline reaction conditions make it possible for salts of the N-benzyl-N-phosphonomethyl-amino-ethanol derivatives also to be used for the reaction. These are neutralized under the alkaline reaction conditions. Examples of these are the hydrochlorides and the methane sluphonates. A large number of derivatives of the compounds of the formula II which are substituted on the ethanol oxygen can also be used for the reaction; examples of these are the O-alkanoyl, in particular acetyl, derivatives of O-benzoyl derivatives. Under the alkaline reaction conditions described, the ester grouping in these derivatives is split and the hydroxymethyl group is thus liberated in situ for the dehydrogenation. The above amount of alkali metal hydroxide must in these cases be increased by 1 mole of alkali metal hydroxide per mole of N-benzyl-N-phosphonomethyl-aminoethanol derivatives.

The process is advantageously carried out under an inert gas atmosphere with exclusion of oxygen. Hydrogen, nitrogen or argon, for example, can be used as the protective gas. It is used for displacing the atmospheric oxygen otherwise present, which could have an adverse influence on the course of the reaction.

The N-benzyl-N-phosphonomethyl-aminoethanol derivatives of the formula II can be prepared by the methods described in Zh. Obsch. Khim. 55, 1744 (1985) or J. Org. Chem. 31, 1603 (1966), if $R^1$ and $R^2$ denote an oxygen-containing containing radical. Further possible methods for the preparation of compounds of the formula II are described in Houben Weyl, Volume XII/1 (1963). There are no high requirements imposed on the purity of these N-benzyl-N-phosphonomethyl-aminoethanol derivatives; they can also be used as crude products in the process according to the invention.

The following example serves to illustrate the invention.

EXAMPLE 1

45.4 g (0.3 mol) of 2-benzylaminoethanol (prepared according to U.S. Pat. No. 2,683,744) and 9.85 g (0.315 mol) of 96% strength paraformaldehyde are mixed and the mixture is heated until the exothermic reaction starts (about 40° C.). When this reaction has subsided, the mixture is stirred at 60° C. for a further 30 minutes, 45 ml of toluene are then added and the water of reaction is then distilled off using a water separator. The heating bath is removed and 41.4 g (0.3 mol) of diethyl phosphite are added dropwise to the hot solution; the mixture is then stirred at 90° C. for 6 hours and the solvent is subsequently distilled off.

The crude N-benzyl-N-(bisethoxyphosphonomethyl)aminoethanol thus prepared, 132 g (1.1 mol) of 33% strength aqueous sodium hydroxide solution and 42 g of water are stirred until a homogeneous solution is formed. the reaction mixture is introduced, together with 20 g of Raney copper (moist weight) and 4 g of palladium oxide catalyst (10% by weight of palladium-on-charcoal), into a 500 ml autoclave, covered with a layer of hydrogen and heated at 170° C. for 2 hours. After the autoclave has been cooled and let down, the catalysts are filtered off. 300 ml of toluene are added, the water is distilled off using a water separator and the toluene is then distilled off.

400 ml of concentrated hydrochloric acid cooled at 0° C. is added to the residue and the sodium chloride which has precipitated out is filtered off and evaporated. The residue is treated with 6 g of active charcoal in 300 ml of boiling water and filtered hot and the filtrate is concentrated to about 50 ml. The N-phosphonomethylglycine which has crystallized out is filtered off and dried. 38 g (75% of theory, based on 2-benzylaminoethanol) of N-phosphonomethylglycine with a purity of >99% are obtained.

I claim:

1. A process for the preparation of N-phosphonomethylglycine of the formula I

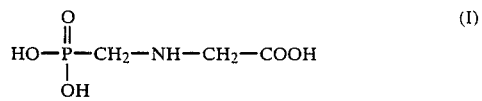

which comprises reacting a compound of the formula II or a salt or ester thereof

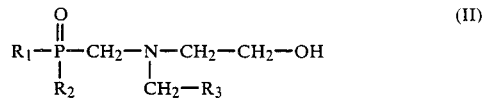

in which
$R_1$ and $R_2$ independently of one another denote hydroxyl or a hydrolyzable radical from the group comprising ($C_1$-$C_6$)alkoxy, ($C_3$-$C_6$)cycloalkoxy, aryloxy, aryl($C_1$-$C_4$)alkoxy, mercapto, ($C_1$-$C_6$)alkylthio, ($C_3$-$C_6$)cycloalkylthio, arylthio, aryl(-$C_1$-$C_4$)alkylthio, amino, mono- or di-($C_1$-$C_6$)alkylamino, arylamino or aryl($C_1$-$C_4$)alkylamino and
$R_3$ denotes aryl,
in a closed reaction vessel in the presence of a dehydrogenation and hydrogenation catalyst with an alkali metal hydroxide or alkaline earth metal hydroxide in water and subsequently adding a mineral acid.

2. The process as claimed in claim 1, wherein $R_1$ and $R_2$ denote hydroxyl or ($C_1$-$C_4$)alkoxy and $R_3$ denotes phenyl, which can be substituted by ($C_1$-$C_4$)alkyl.

3. The process as claimed in claim 1 which is carried out in the presence of an alkali metal hydroxide.

4. The process as claimed in claim 1, which is carried out at temperatures between 120° C. and 200° C.

5. The process as claimed in claim 1, which is carried out at temperatures between 160° C. and 180° C.

6. The process as claimed in claim 1, wherein cadmium oxide, zinc oxide, copper or a copper/zirconium mixed catalyst is used as the dehydrogenation catalyst.

7. The process as claimed in claim 1, wherein palladium, platinum or nickel is used as the hydrogenation catalyst.

8. The process as claimed in claim 1, wherein a combination of copper with palladium or platinum is used as the catalyst.

9. The process as claimed in claim 1, wherein the molar ratio alkali or alkaline earth metal hydroxide to the compound of the formula II is greater than or equal to 3.

10. The process as claimed in claim 1, which is carried out under an inert gas atmosphere in an autoclave.

* * * * *